(12) United States Patent
Sturm

(10) Patent No.: US 7,005,639 B2
(45) Date of Patent: Feb. 28, 2006

(54) SYSTEM AND METHOD OF COMPOSITION CORRECTION FOR BETA GAUGES

(75) Inventor: Steven Perry Sturm, Dublin, OH (US)

(73) Assignee: ABB Inc., Columbus, OH (US)

( * ) Notice: Subject to any disclaimer, the term of this patent is extended or adjusted under 35 U.S.C. 154(b) by 259 days.

(21) Appl. No.: 10/628,197

(22) Filed: Jul. 28, 2003

(65) Prior Publication Data

US 2005/0023464 A1    Feb. 3, 2005

(51) Int. Cl.
*G01N 23/00* (2006.01)
(52) U.S. Cl. .................................................... 250/308
(58) Field of Classification Search ............... 250/308, 250/252.1, 358.1
See application file for complete search history.

(56) References Cited

U.S. PATENT DOCUMENTS

| | | |
|---|---|---|
| 2,988,641 A | 6/1961 | Gough |
| 3,087,061 A | 4/1963 | Dukes et al. |
| 3,210,545 A | 10/1965 | Bennett |
| 4,047,029 A | 9/1977 | Allport |
| 5,099,504 A | 3/1992 | Pettit |
| 5,233,195 A | 8/1993 | Hellstrom et al. |
| 5,778,041 A | 7/1998 | Chase et al. |
| 5,854,821 A | 12/1998 | Chase et al. |
| 6,498,646 B1 | 12/2002 | Typpo et al. |
| 2004/0155196 A1 * | 8/2004 | Typpo ..................... 250/358.1 |

FOREIGN PATENT DOCUMENTS

| | | |
|---|---|---|
| EP | 1 447 659 A2 | 8/2004 |
| WO | WO 94/29700 A1 | 12/1994 |

OTHER PUBLICATIONS

Steven P. Sturm; A new generation of beta gauges; Papex International Conference; Nov. 1993; Maastricht Netherlands.

* cited by examiner

*Primary Examiner*—David Porta
*Assistant Examiner*—Mindy Vu
(74) *Attorney, Agent, or Firm*—Stevens & Showalter LLP

(57) ABSTRACT

Beta gauge composition correction is performed using signals from a plurality of detectors that are positioned so that the ratio of radiation received by the detectors depends on the composition of material through which the radiation passes before reaching the detectors. Radiation is measured at the detectors and the differences between radiation received by the detectors is used to compensate the beta gauge to correct for composition variations. An array of detectors is divided into inner detectors generally aligned with the central portion of a beta radiation beam and at least one set of outer detectors surrounding, at least in part, the inner detectors. Measurements are made including all the detectors, the inner detectors and the at least one set of outer detectors with the difference between the measurements made by the inner detectors and the outer detectors being used to compensate the total measurement made by all the detectors.

20 Claims, 5 Drawing Sheets

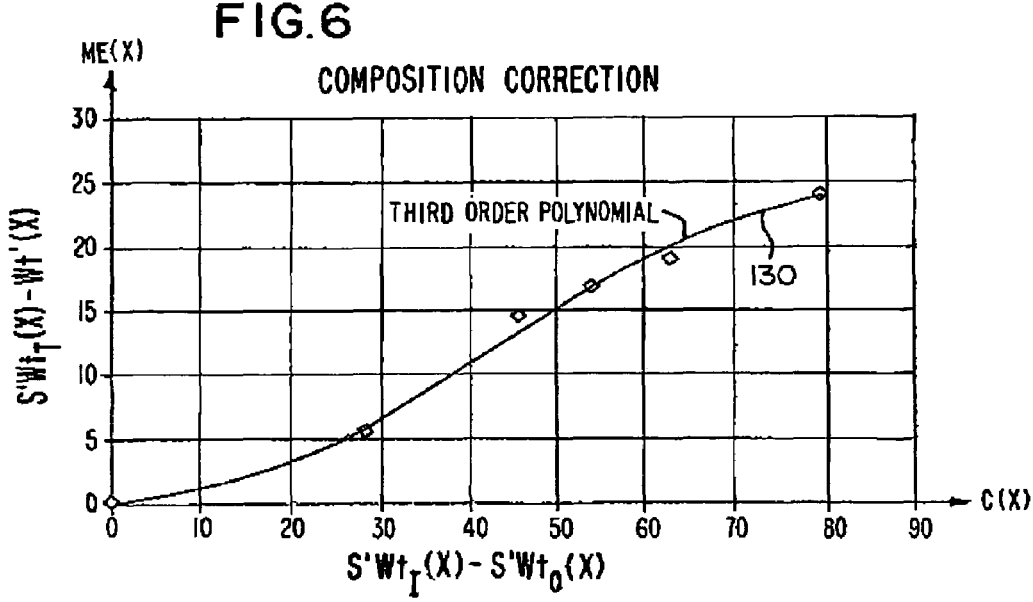
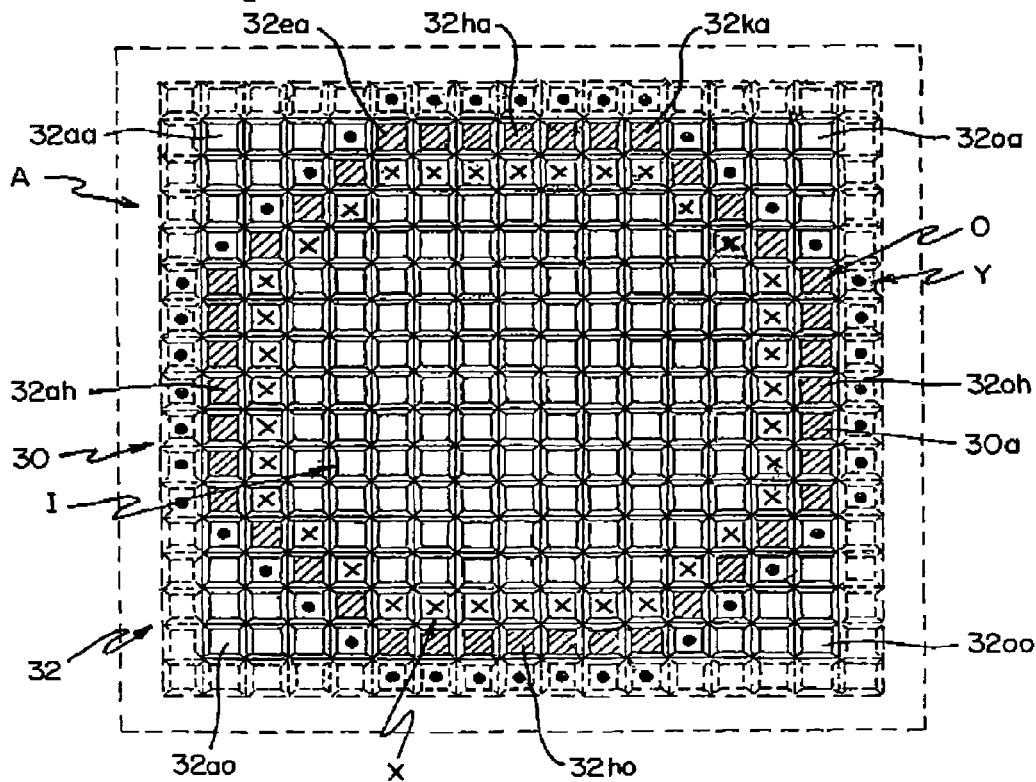

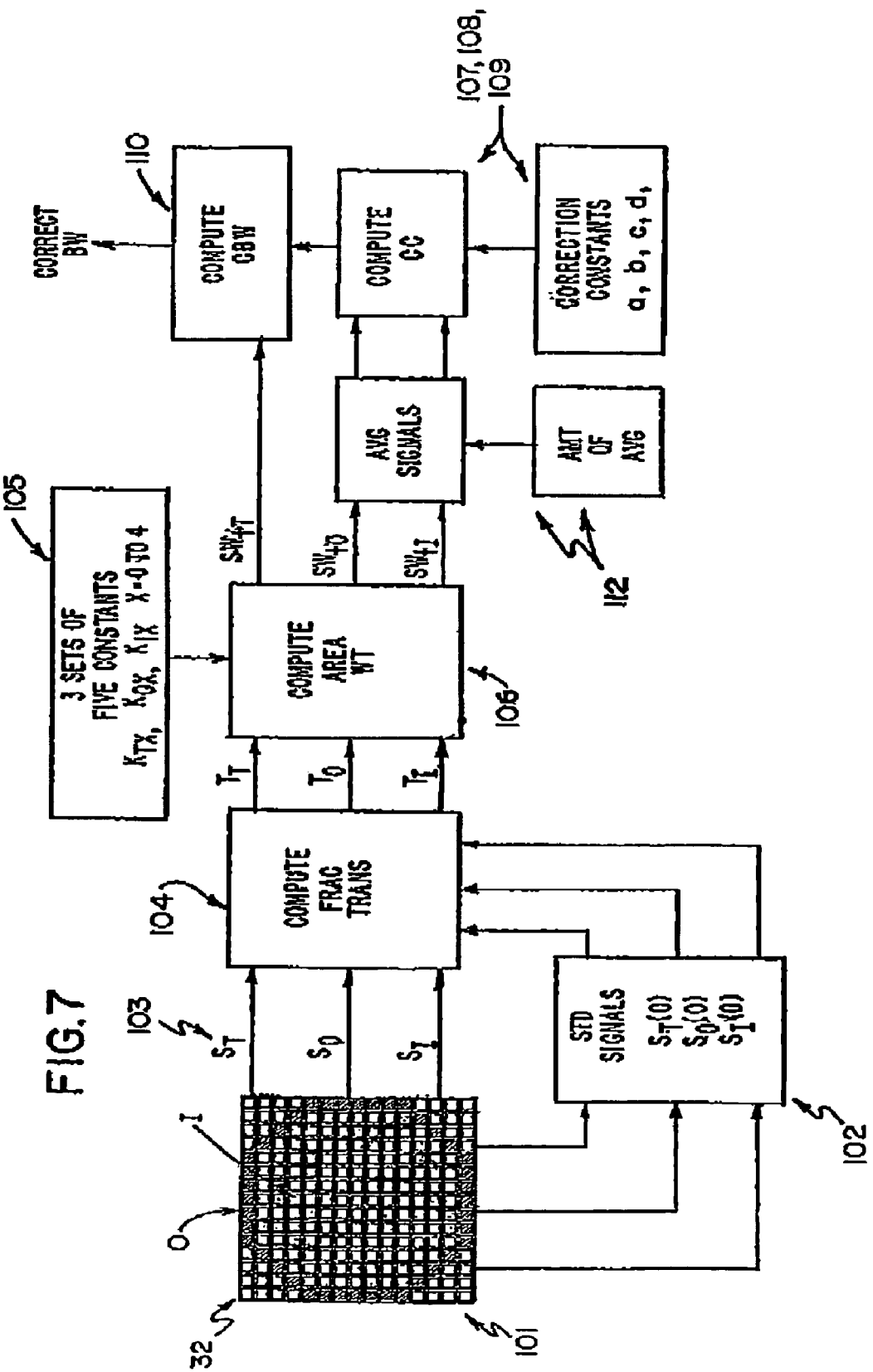

SYSTEM AND METHOD OF COMPOSITION CORRECTION FOR BETA GAUGES

FIELD OF THE INVENTION

The invention of the present application relates in general to measuring characteristics of a web of material as it is being manufactured and, more particularly, to a system and method for on-line compensation of a beta gauge to better measure webs wherein the atomic composition of the web may change during manufacture. While the invention is generally applicable to manufacture of a variety of webs, it will be described herein with reference to a beta gauge for measuring basis weight of a web of paper as it is being manufactured for which it is particularly applicable and initially being used.

BACKGROUND OF THE INVENTION

Sensors used in process control systems for measuring basis or area weight of a web of paper need to develop accurate measurement information for a quickly moving, fluttering web, while operating in a high humidity, dirty, hot and/or wet environment. These sensors are usually mounted on measurement platforms that scan the sensors slowly in a cross-process direction as the process web (web of paper) moves relatively rapidly in a process direction. Although beta instruments (or beta gauges) are relatively insensitive to the atomic composition of the measured material, they have enough composition sensitivity to cause correlation errors when used to measure paper basis weight in the presence of varying amounts of additives like clay, chalk or titanium dioxide, $TiO_2$. Beta instrument suppliers have developed methods to reduce the composition sensitivity of the beta instruments, generally using a nuclear diffuser or backscatter generator. However, as the beta instrument is made more insensitive to composition, the signal to noise ratio is reduced.

Accordingly, there is a need for a system and method that provides on-line compensation of a beta gauge for atomic composition changes in a web being manufactured, for example a paper web, without substantial reduction in signal to noise ratio.

SUMMARY OF THE INVENTION

This need is met by the invention of the present application wherein a system and method of composition correction for a beta gauge processes signals from a plurality of detectors. The detectors are positioned so that the ratio of beta radiation received by the detectors is dependent on the composition of material through which the beta radiation passes before being received by the detectors. Beta radiation is measured at the detectors and the differences between the beta radiation received by the detectors is used to compensate the beta gauge to correct for composition variations. In the illustrated embodiment, an array of detectors is used with the array being divided into inner detectors generally aligned with the central portion of a beta radiation beam and outer detectors surrounding, at least in part, the inner detectors. The outer detectors can be configured into one, two or more groupings of detectors. Measurements are made including all the detectors (or all of the detectors that are used), the inner detectors and the outer detectors with the difference between the measurements made by the inner detectors and the outer detectors being used to compensate the total or combined measurement made by all the detectors (or all of the detectors that are used).

BRIEF DESCRIPTION OF THE DRAWINGS

The benefits and advantages of the present invention will become apparent to those skilled in the art to which this invention relates from the subsequent description of the illustrated embodiments and the appended claims, taken in conjunction with the accompanying drawings, in which:

FIG. 2b shows a side view of the array of solid-state radiation detectors of FIG. 2a;

FIG. 6 graphically shows the composition correction in accordance with the present invention;

FIG. 7 is a block diagram of an overall system operable in accordance with the present invention; and FIG. 8 shows an alternate embodiment of a receiving face of an array of solid-state radiation detectors for use in the present invention including three outer sets of detectors.

DETAILED DESCRIPTION OF THE INVENTION

Figure 1:
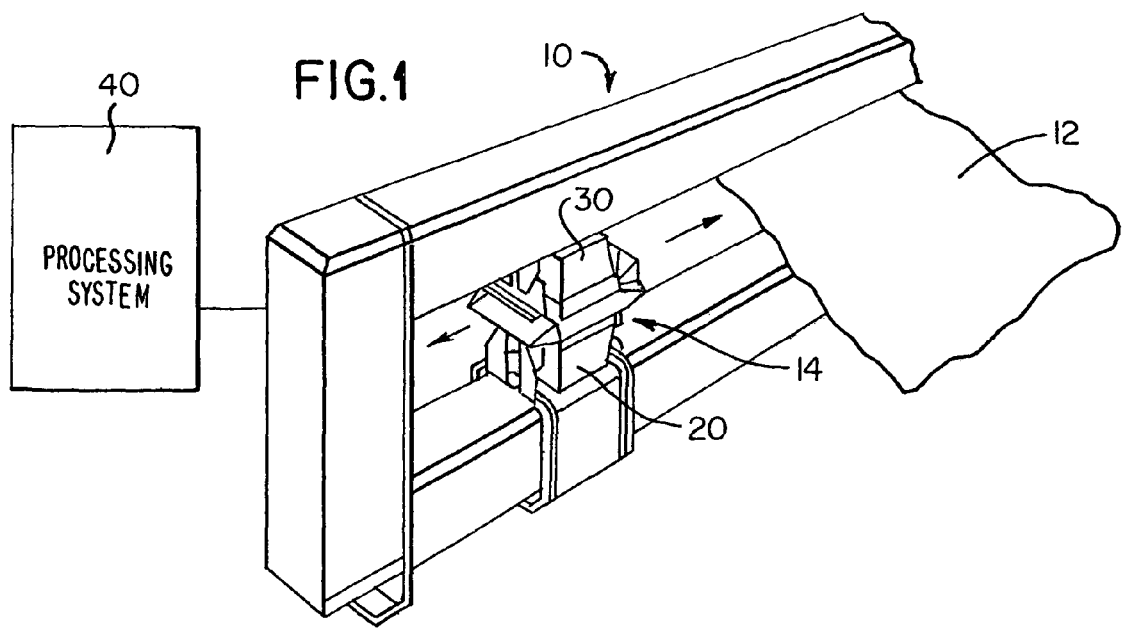
FIG. 1 shows an apparatus for measuring the basis weight of a web product that can be operated in accordance with the present invention.

Referring now to the drawings, wherein like-referenced characters indicate corresponding elements throughout the several figures, attention is first drawn to FIGS. 1, 2a, 2b and 3 that show an embodiment of a beta gauge made and operable in accordance with the present invention that is mounted on a conventional scanner 10 for measuring characteristics of a web product. While the present invention is generally applicable to measurement of a variety of web products, the present invention will be described herein with reference to the manufacture of a paper web 12 for which it is particularly applicable and initially being used. Measuring apparatus 14 includes a beta radiation source assembly 20, a detector assembly 30 and a processing system 40.

The source assembly 20 includes a beta radiation source 22 and utilizes a collimator or aperture plate 24 that shapes the radiation beam in the detector plane 30p within the detector assembly 30. For example, an aperture plate 24 having a circular aperture results in a circular beam in the detector plane 30p. For the invention of the present application, two solid-state radiation detectors may be used and it is desirable to have the detectors have the same general shape as the radiation beam in the detector plane 30p. For example for a circular beam, the solid-state radiation detectors may include a circular center detector and an outer ring-shaped or annular detector that surrounds the circular center detector.

Figure 2A:
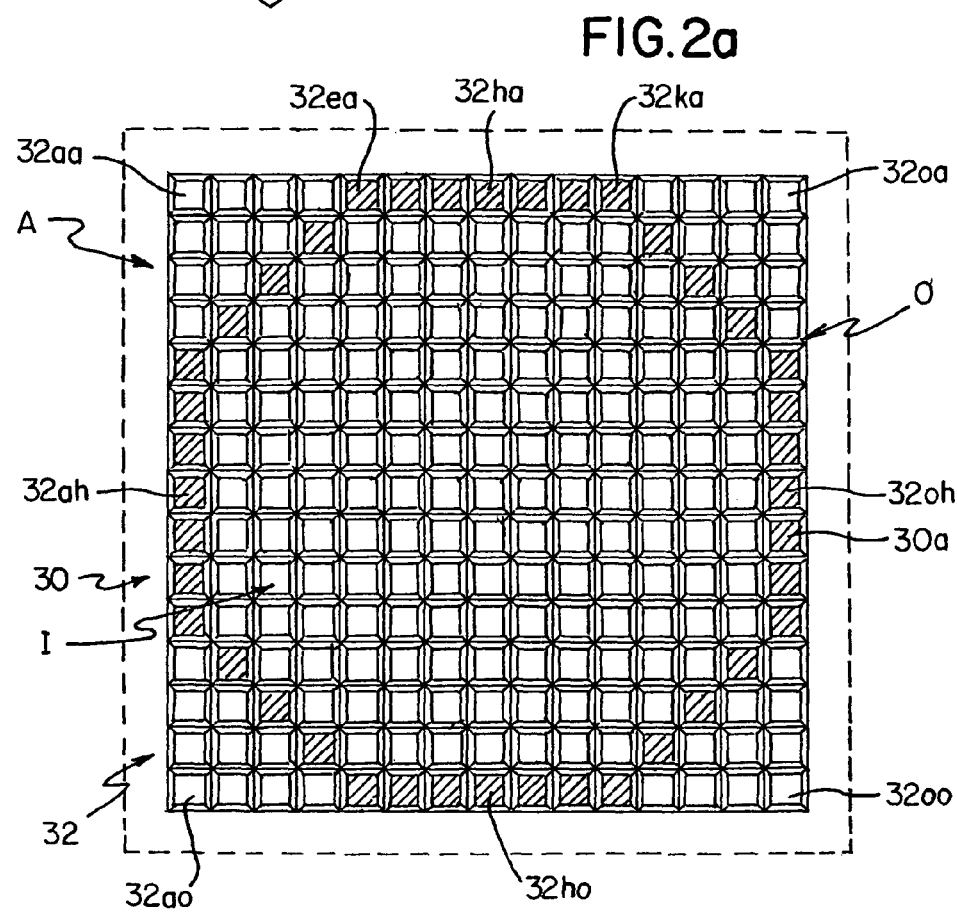
FIG. 2a shows the receiving face of an array of solid-state radiation detectors for use in the present invention.
Figure 2B:
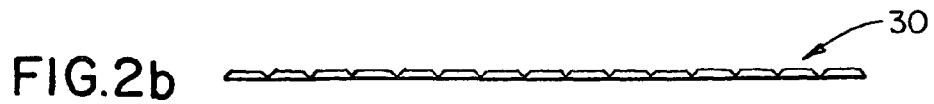

To avoid the use of costly custom detectors, a plurality of standard solid-state radiation detectors 32 are used in the present invention to approximate the shape of the beam. For example in the illustrative embodiment of FIGS. 2a, 2b, the radiation detectors 32 comprise a 15×15 array A of square solid-state PIN radiation detectors that are used to detect beta radiation. Beta radiation detectors, such as the radiation detectors 32 of FIGS. 2a, 2b, are commercially available from MOXTEK, Inc. of Orem, Utah. In FIG. 2a, the radiation detectors 32 are labeled 32aa to 32oo (first subscript corresponding to the column of the array A and second subscript corresponding to the row of the array A). The individual detectors 32 can be assigned to correspond to a given system configuration. Individual signals are generated by the detectors 32 and these signals can be combined by either electrically connecting selected ones of the detectors 32 together or by combining selected signals using software in the processing system 40. For example, a first or inner signal can be generated from inner detectors generally aligned with the beam and generally centered in the array, and at least one second or outer signal can be generated from one or more groupings of detectors, in the illustrated embodiment generally surrounding the inner detectors. As should be or will become apparent, the configuration of the measurement system is more easily modified if the combination of selected groupings of the detector signals is performed in the processing system 40 so such software combination is currently preferred.

Figure 3:
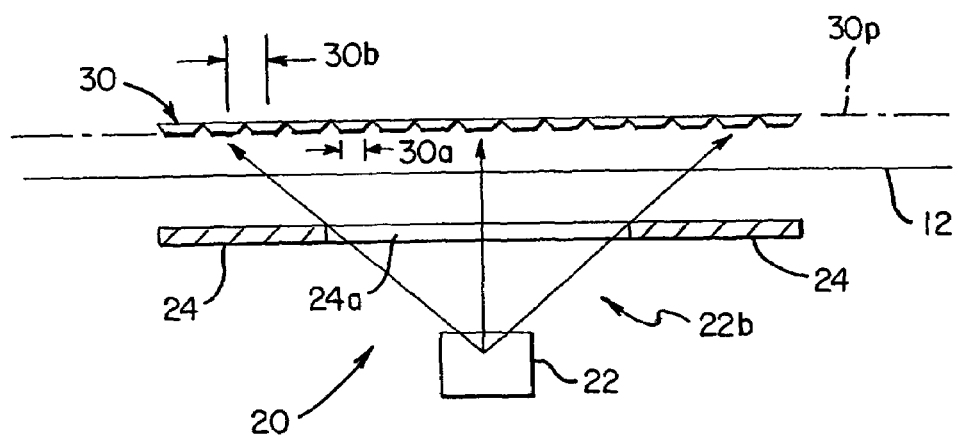
FIG. 3 shows a side view of the system of the present invention including the array of solid-state detectors of FIGS. 2a and 2b.

As illustrated in FIG. 2a, one assignment of individual detectors of the 15×15 array A includes 40 outer rings detectors O [32ea, 32fa, 32ga, 32ha, 32ia, 32ja, 32ka—top row], [32lb, 32mc, 32nd—diagonal], [32oe, 32of, 32og, 32oh, 32oi, 32oj, 32ok—right side column], [32nl, 32mm, 32ln diagonal], [32ko, 32jo, 32io, 32ho, 32go, 32fo, 32eo—bottom row], [32dn, 32cm, 32bl—diagonal], [32ak, 32aj, 32ai, 32ah, 32ag, 32af, 32ae—left side column], and, [32bd, 32cc, 32db—diagonal] oriented around the outside of the array A to approximate an outer annular detector. Inner detectors I, located within the 40 detectors O, approximate an inner circular detector. As shown in FIGS. 2 and 3, each of the radiation detectors 32 may have an active area 30a of 1.0 mm by 1.0 mm and may be placed on 1.35 mm centers 30b. Preferably all of the detectors 32 have substantially the same dimensions.

In the illustrated embodiment, the placement of the individual detectors 32, the intensity of the source beam 22b, the shape and/or size of the collimating aperture 24a and the assignments of the individual detectors 32 to either the inner detectors I or the outer detectors O are coordinated so that the inner detectors I detect approximately ninety-five percent of the available signal while the outer detectors O detect approximately five percent of the available beta signal with nothing between the source and detector. Thus, the outer detectors O are located substantially on the outer most edge of the incident radiation. Other detector, source, aperture and detector assignment arrangements providing ranges of approximately ninety-nine percent of the beta signal being detected by the inner detectors I and approximately one percent of the beta signal being detected by the outer detectors O to approximately seventy percent of the beta signal being detected by the inner detectors I and approximately thirty percent of the beta signal being detected by the outer detectors O are contemplated for use in the present invention. Also, while the outer detectors O are illustrated as completely surrounding the inner detectors I, there may be one or more gaps in the outer detectors O so that the inner detectors I are only partially surrounded.

The invention of the present application relies on the fact that the energy distribution of the beta particles in the detector plane 30p changes with the composition of the web 12. In particular, when high atomic number elements exist in the web 12, the distribution of higher energy beta particles increases at the outermost edge of the detectors 32, i.e., at the outer detectors O, relative to the center detectors, i.e., the inner detectors I. Calculations based on measuring the changing distribution are used to generate a correction signal that is used to compensate for composition sensitivity of the radiation detectors 32.

Figure 4:
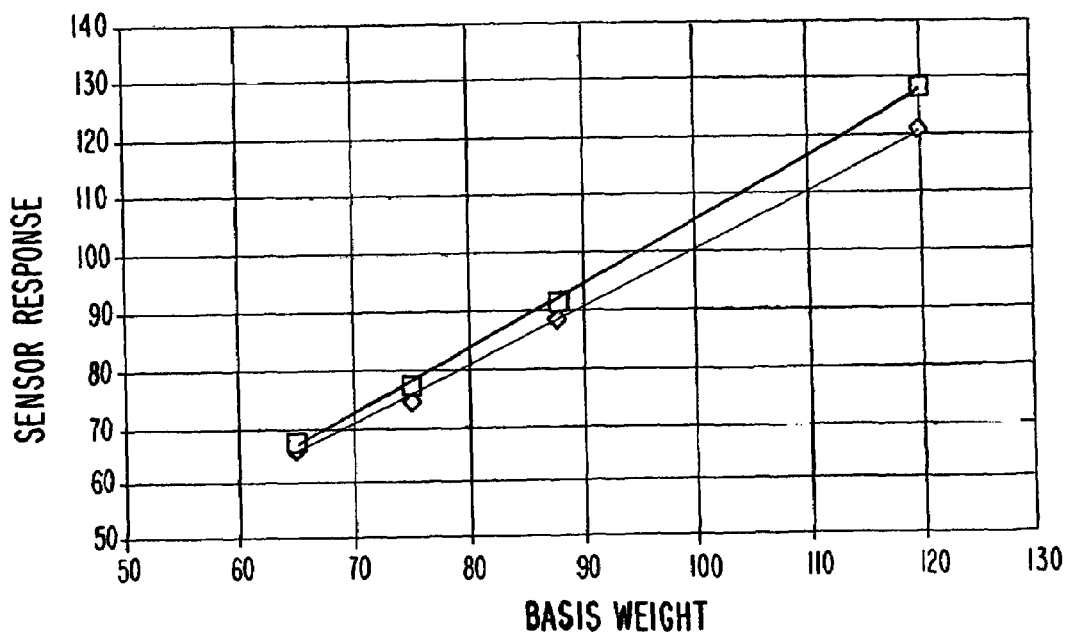
FIG. 4 graphically shows the overall sensor response if all the detectors in FIG. 2 are used with equal weighting.

FIG. 4 shows the overall sensor response if all the detectors in FIG. 2a are used with equal weighting. The linear response for the sample (□) having high atomic number additives (high ash), such as clay, calcium carbonate, and titanium dioxide, $TiO_2$, for example, has a greater slope since, for a given basis weight, the sensor response is higher than it is for a sample (◇) having no additives. The greater slope occurs due to the effective absorption coefficient of the material being measured. For pure exponential absorption, there is a single absorption coefficient. In practice, the absorption coefficient varies somewhat with process weight requiring higher order algorithms to compute weight from the percentage of the beta signal that is transmitted through a sample (percent transmission). However, a good first approximation is to assign an absorption coefficient corresponding to a type of material.

If two materials have a different absorption coefficient, then a measurement slope difference, as shown in FIG. 4, is apparent. The effective absorption coefficient varies as a function of the effective atomic number (atomic number is generally associated with an element, like Titanium (Z-22), but paper is a mixture of elements for which an effective atomic number (or atomic weight) can be computed, see *Measurement and Detection of Radiation* by Tsoulfanidis, ISBN: 1560323175, page 130) of the material being monitored since materials with a higher atomic number have slightly increasing effective absorption coefficients when measured using a simple (uncompensated such as by diffusers or backscatter components) collimated beam of beta radiation. This increase in effective atomic number and increase in effective absorption coefficient causes the response of a sensor to show a higher reading for a first one of two samples having a higher effective atomic number than a second one of the two samples even though the two samples have the same area weight.

Figure 5:
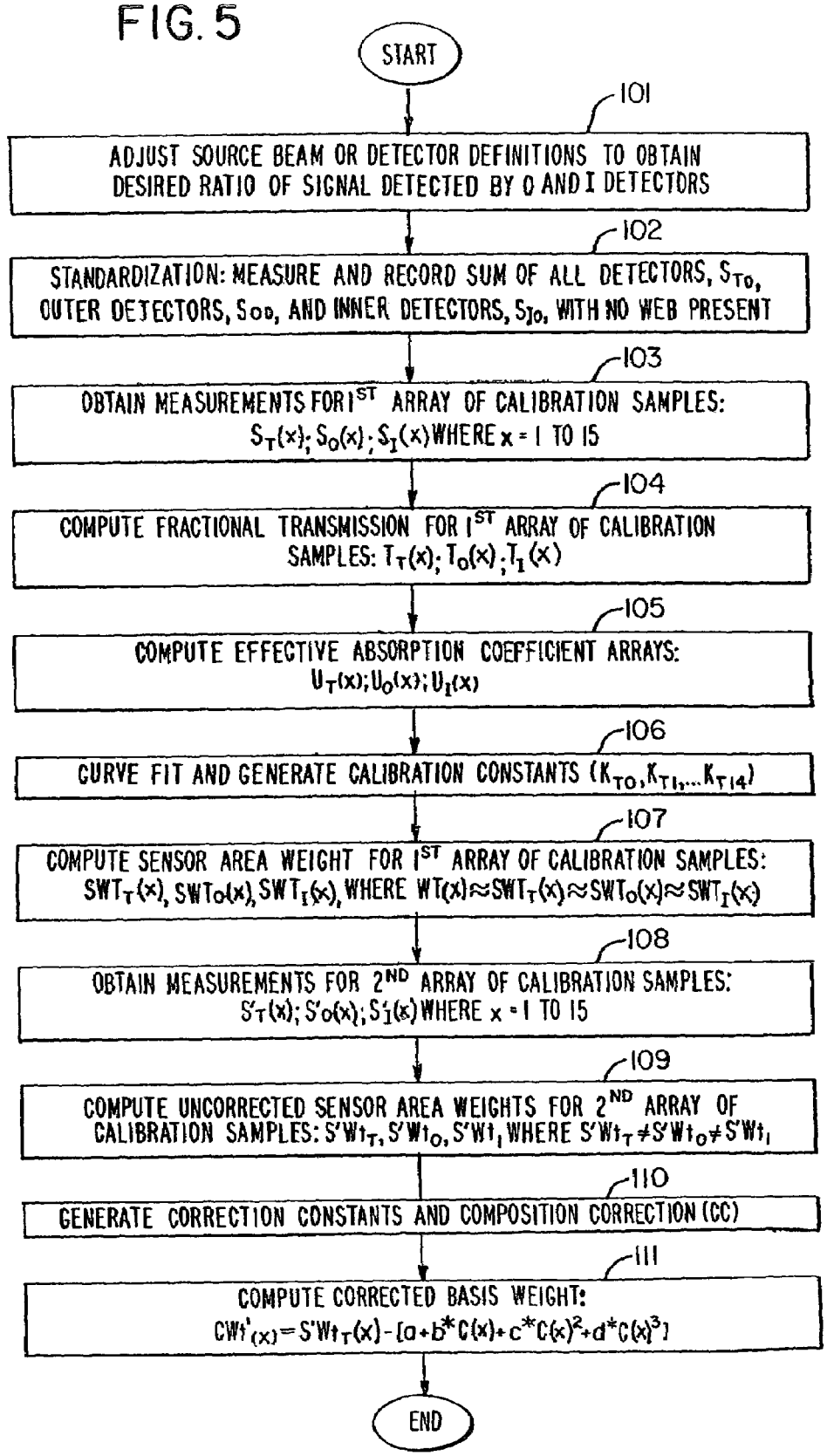
FIG. 5 is a flowchart showing an illustrative embodiment of calibration of the apparatus of the present application.

FIG. 5 is a flowchart illustrating a technique for calibration of the compensation correction system of the present application. While calibration is contemplated as normally being performed during manufacture of the system using samples as described below, calibration can also be performed at a web manufacturing site with comparable samples or samples generated by a user at the web manufacturing site. On site calibration may be desirable for some users, particularly those producing webs having unusual additives compared to clay, calcium carbonate, or titanium dioxide, i.e., flat sheet processes outside the paper industry. Reference should also be made to FIG. 7 that is a block diagram of an overall system operable in accordance with the present invention. Many of the reference numerals in FIG. 7 correspond to steps taken in FIG. 5 for calibration purposes as will be apparent.

An initial calibration step is performed in step 101 with an air gap, i.e., no material, between the source 22 and the detector assembly 30. As described above, the system is adjusted to provide a measurement beam and detector assignment (either hardware electrical detector interconnections or software combinations) wherein the inner detectors I detect approximately ninety-five percent of the beam while the outer detectors O detect approximately five percent of the beam. Of course, detection of different percentages by the inner detectors I and the outer detectors O is contemplated for use in the present invention. Detector patterns and detection percentages are easily changed in the illustrated embodiment by means of detector selection—for the illustrated embodiment, selecting different detectors in the array to be included in either the inner detectors I or the outer detectors O.

The remaining unused ones of the detectors 32 (see 32aa, S2oa, 32oo and 32ao in FIG. 2a as examples), i.e., detectors that are not used to define either the inner detectors I or the outer detectors O, may be included as additional detectors in the outer detectors O or may be used as part of the total or combined arry signal based on all the detectors or, particularly for circular symmetric beams, may be ignored. These detectors add versatility to the detector array A to fine tune the ratio of signal detected by the outer detectors O or the inner detectors I. It may be possible to exclude these detectors for given applications and to reduce costs of the detector assembly 30. Step 101 is accomplished by either adjusting individual detector elements that are included in either the outer detectors O or the inner detectors I and/or by adjusting the amount of collimation of the beta beam via the collimator 24 shown in FIG. 3.

In the standardization step 102 of FIG. 5, three signals are measured:

$S_{T0}$ is based on the measured values of all the detectors 32 (or all the detectors being used) of the array A of FIG. 2;

$S_{O0}$ is based on the measured values of all the outer detectors O of the array A of FIG. 2; and $S_{I0}$ is based on the measured values of all the inner detectors I of the array A of FIG. 2. It is noted that if the unused detectors are excluded, then $S_{T0}$ is based on the measured values of all the outer detectors O and all the inner detectors I.

In step 103, sensor measurements are taken on a first array of calibration samples of a material that is pure carbohydrate with no high atomic number additives. This material can be pure cellulose or other more durable synthetic carbohydrate such as Mylar®, a material developed by Dupont Corporation. The array of first calibration samples have laboratory area weight assignments, Wt(x), determined via normal laboratory gravimetric methods. The following signal arrays are taken using the first sample array:

$S_T(X)$ is an array of signal values of all the detectors 32 (or all detectors being used) of the detector array A of FIG. 2 for the first array of calibration samples;

$S_O(x)$ is an array of signal values of all the outer detectors O of the detector array A of FIG. 2 for the first array of calibration samples; and $S_I(x)$ is an array of signal values of all the inner detectors I of the detector array A of FIG. 2 for the first array of calibration samples.

Where x=1 to 15 for an array of 15 calibration samples having laboratory area weight assignments Wt(x). It is noted that the number of samples used and hence the range of the sample array may be varied above and below 15 to provide the confidence level required for a given application.

In step 104, each of the above signal arrays, $S_T(X)$, $S_O(x)$, and $S_I(x)$, are used to calculate arrays of fractional transmission values (fractional transmission is the ratio of transmission through a sample having t thickness $T_t$ to transmission through a sample having 0 thickness $T_0$, i.e., an air gap, such that $T=T_t/T_0$) as follows:

$$T_T(x)=S_T(x)/S_{T0}$$

$$T_O(x)=S_O(x)/S_{O0}$$

$$T_I(x)=S_I(x)/S_{I0}$$

The fractional transmission of a material decreases as the basis weight of the material increases.

In step 105, effective absorption coefficient arrays are calculated for each sample of the first array of calibration samples using each transmission value and each laboratory value of the first array of calibration samples as follows:

$$U_T(x)=-\ln(T_T(x))/Wt(x)$$

$$U_O(x)=-\ln(T_O(x))/Wt(x)$$

$$U_I(x)=-\ln(T_I(x))/Wt(x)$$

Where:

Wt(x) is the laboratory area weight array for the first array of calibration samples; and $U_T(x)$, $U_O(x)$ and $U_I(x)$ are the effective absorption coefficient arrays corresponding to samples in the first array of calibration samples, for instance for x=1 to 15.

In step 106, a multiple least-square-curve fit is performed to model a predicted absorption coefficient. In a pure exponential absorber, the area weight (basis weight) is computed using a measured transmission signal and a known absorption coefficient for the material under test. The Beer-Lambert law states that fractional transmission $T=e^{-\mu w}$ where T is fractional transmission $(T_t/T_0)$;

$\mu$ is absorption coefficient (m$^2$/g); and w is the area weight (g/m$^2$).

Area weight can be determined by using the Beer-Lambert law, $w=-\ln T/\mu$. However, for beta transmission, the Beer-Lambert law is only an approximation, so $\mu$ is defined as a function of T since $\mu$ varies as weight varies. To minimize the percent error in the computed area weight, a multiple least-square-curve fit is used to model a predicted absorption coefficient based on a fourth order polynomial with the natural logarithm of the fractional transmission T as the independent variable and the absorption coefficient $\mu$ as the dependent variable. Three curve fits are conducted: one for all of the array detectors (or all of the detectors that are used), the total T detector array; one for the inner detectors, the I detector array; and, one for the outer detectors, the O detector array. The arrays used for the curve fits, to generate five calibration coefficients for each detector array, are defined above with reference to steps 104 and 105.

The form of the predicted absorption coefficient $U_p$ polynomial curve fit is:

$$U_pZ(x)=K_0+K_1*\ln Tz(x)+K_2*(\ln Tz(x))^2+K_3*(\ln Tz(x))^3+K_4*(\ln Tz(x))^4$$

Where z is T, O, or I as shown in steps 104 and 105.

This results in the general equation for converting measured fractional transmission into sensor computed area weight for any detector array being:

$$SWt=-\ln T/[K_0+K_1*\ln T+K_2*(\ln T)^2+K_3*(\ln T)^3+K_4*(\ln T)^4] \quad\text{(Eq. 1)}$$

Where:

SWt is the sensor computed area weight;

T is the measured fractional transmission of a detector array (T, O or I); and $K_0$, $K_1$, $K_2$, $K_3$, $K_4$ are calibration constants found by the multiple least-square-curve fit described above, a different set for each detector array (T, O and I).

While these procedures will be apparent to those skilled in the art, additional information regarding the mathematics involved in generation of the calibration constants can be obtained by reference to mathematical textbooks or to technical computing software programs, such as MatLab by The MathWorks of Natick, Mass. The curve fits and the generation of calibration constants are performed for all three signal arrays: $S_T(x)$, $S_O(x)$, and $S_I(x)$ so that the sensor computed area weights $SWt_T$, $SWt_O$ and $SWt_I$ are as shown in the following equations:

$$SWt_T = -\ln T_T/[K_{T0} + K_{T1} * \ln T_T + K_{T2} * (\ln T_T)^2 + K_{T3} * (\ln T_T)^3 + K_{T4} * (\ln T_T)^4]$$

$$SWt_O = -\ln T_O/[K_{O0} + K_{O1} * \ln T_O + K_{O2} * (\ln T_O)^2 + K_{O3} * (\ln T_O)^3 + K_{O4} * (\ln T_O)^4]$$

$$SWt_I = -\ln T_I/[K_{I0} + K_{I1} * \ln T_I + K_{I2} * (\ln T_I)^2 + K_{I3} * (\ln T_I)^3 + K_{I4} * (\ln T_I)^4]$$

Thus, fifteen calibration constants $K_{T0}$, $K_{T1}$, $K_{T2}$, $K_{T3}$, $K_{T4}$, $K_{O0}$, $K_{O1}$, $K_{O2}$, $K_{O3}$, $K_{O4}$, $K_{I0}$, $K_{I1}$, $K_{I2}$, $K_{I3}$, $K_{I4}$, are generated for a web sample that is 100% organic carbohydrates, such as cellulose or Mylar®. If the first array of calibration samples is re-measured, (transmission values measured for each sample and calibrated weight calculations made in accordance with Equation 1) then three area weight measurement arrays are generated, $SWt_T(x)$, $SWt_O(x)$, $SWt_I(x)$. And, the three area weight measurement arrays substantially agree (a small amount of laboratory uncertainty and nuclear noise contribute to small differences in each reading) with the laboratory values assigned to the first array of calibration samples, $Wt(x)$, and substantially agree with each other, $Wt(x) \approx SWt_T(x) \approx SWt_O(x) = SWt_I(x)$ as shown in step 107. It is noted that a different, alternate array of calibration samples, having the same composition and weight range as the first array of calibration samples, may be measured rather than re-measuring the first array of calibration samples to verify the calibration constants.

Once these calibration constants $K_{T0}$–$K_{I4}$ have been determined, additional measurements of other Mylar® samples should result in area weight measurements that substantially agree with laboratory area weight measurement for each of the three measurements, i.e., $SWt_T \approx SWt_O \approx SWt_I \approx$ gravimetric weight. $SWt_T$ is also defined as a "fast" uncorrected sensor measurement signal since the signal has not been filtered and has a response defined by either the detector time constant or the system analog-to-digital sampling rate.

After using the first array of calibration samples to derive the fifteen constants $K_{T0}$–$K_{I4}$ as described above, a second array of calibration samples, preferably of the same number and having approximately the same laboratory area weight range as the first set of samples, are measured in step 108 and processed in steps 109 and 110. The second array of calibration samples has a higher effective atomic number compared to the first set of samples and may be cellulose filled with titanium dioxide, calcium carbonate, and/or clay as well as other materials or combinations of these materials. Since the changes in atomic number are relatively small for typical fill values of these commonly used materials, the second set of samples is preferably made from pure aluminum. While other materials having higher atomic number can be used, aluminum is currently believed to provide the best results for the illustrated paper monitoring application. For aluminum samples, the effective atomic number is the same as a 100% calcium carbonate fill or a 60% titanium dioxide fill. The second calibration sample array has laboratory area weights $Wt'(x)$ assigned using typical laboratory gravimetric analysis. The area weight measurements or weight arrays $S'Wt_T(x)$, $S'Wt_O(x)$ and $S'Wt_I(x)$, taken on the array of second calibration samples using the above described techniques employing the constants $K_{T0}$–$K_{I4}$ and equation 1 are not equal to the laboratory weight array $Wt'(x)$ of the second calibration samples array. In fact, they differ substantially from the laboratory weight array $Wt'(x)$ of the second calibration set, i.e., $Wt'(x) \neq S'Wt_T(x) \neq S'Wt_O(x) \neq S'Wt_I(x)$.

With reference to FIG. 6, the difference between the measurements $S'Wt_I(x)$ and $S'Wt_O(x)$, referred to as the correction signal array, $C(x) = S'Wt_I(x) - S'Wt_O(x)$, and the difference between the computed basis weight array $S'Wt_T(x)$ and the laboratory array for the second set, $Wt'(x)$, referred to as the measurement error array, $ME(x) = S'Wt_T(x) - Wt'(x)$, are used to determine a composition correction algorithm.

The composition correction algorithm generates values that are subtracted from the basis weights computed from the total T detector array to obtain correct basis weight values. The relationship between the correction signal array $C(x)$ and the measurement error array $ME(x)$ for the array of second calibration samples are apparent in FIG. 6 wherein $C(x)$ is plotted on the X-axis and $ME(x)$ is plotted on the Y-axis.

Referring to FIG. 6, it is noted that the correlation between the correction signal and the measurement error is not linear. Accordingly, a non-linear correction algorithm may be derived for composition correction over a broad range of measurement errors. In the illustrated embodiment, a third order polynomial 130 is used to fit the correction signal array $C(x)$ to the measurement error array $ME(x)$ for the array of second calibration samples. Using these data derived from readings taken on the array of second calibration samples, the curve fit is performed as:

$$ME(x) = a + b*C(x) + c*C(x)^2 + d*C(x)^3 \quad \text{(Eq. 2)}$$

Where a, b, c, and d are constants based on curve fitting. In step 111, a compensated or correct area or basis weight $CWt'(x)$ determination is made using the following equation based on data from the basis weight measurements array of the second calibration samples:

$$CWt'(x) = S'Wt_T(x) - ME(x) = S'Wt_T(x) - [a + b*C(x) + c*C(x)^2 + d*C(x)^3] \quad \text{(Eq. 3)}$$

Using equation 3, a compensated basis weight having good correlation to the laboratory basis weight can be determined, with some small residual laboratory error or uncertainty due to nuclear statistics in each measurement, so that:

$$CWt'(x) \approx Wt'(x)$$

The equation works well over a broad range of variation in atomic composition for additives having atomic number between 4 and 22. For processes having higher atomic number additives the atomic composition of the array of second calibration samples is modified to better match the additives having higher atomic numbers and new a, b, c, and d constants are determined. A block diagram of the entire signal-processing concept is shown in FIG. 7.

The web measurement signals may be filtered or averaged before the composition correction curve is generated or the derived correction signal can be filtered or averaged before being applied to web measurement signal $S'Wt_T$, see 112 in FIG. 7. Filtering of the correction signals (prior to correcting $S'Wt_T$) to remove noise is acceptable because composition variation in typical web manufacturing processes, such as the paper making process, changes very slowly. Averaging reduces the random noise, due for example to nuclear statistics, on the corrected signal.

Once the calibration steps of the flowchart of FIG. 5 are performed for a given instrument, the system provides the correct basis weight for the web of material based on the beta gauge readings as compensated by the above method.

Although the above disclosure is based on the use of an array of detectors having an overall array size of 15×15 with each detector being a one millimeter square cell, it is understood that other sizes and geometries of both arrays and detectors may be used in accordance with the teachings of the present application. For example, a sensor based on circular geometry may have a circular inner detector surrounded by an annular outer detector that partially or wholly rings the circular inner detector. Any arrangement that employs solid-state PIN radiation detectors to separately detect transmitted radiation at different spatial locations in the detector plane is within the scope of the present invention.

It is also possible to provide two or more sets of outer detectors. For example in the embodiment illustrated in FIG. 8, three sets of outer detectors are provided: the original set of outer detectors O; an outer set of detectors X located within the original set of outer detectors O; and, an outer set of detectors Y (individually indicated by the symbol •) located outside the original set of outer detectors O. Of course, the additional sets of outer detectors could all be added outside the original set of outer detectors O or other arrangements of detectors can be provided as will be apparent to those skilled in the art. As illustrated in FIG. 8, by using the outer set of detectors X and the original outer set of detectors O, the compensated or correct area or basis weight CWt"(x) determination includes two correction factors, one determined using the set of outer detectors X as described above and the other determined from the original set of outer detectors O as described above so that the following equation based on data from the basis weight measurements array of the second calibration samples becomes:

$$CWt''(x) = S''Wt_T(x) - ME''(x)$$

$$CWt''(x) = S''Wt_T(x) - [a + b*C_1(x) + c*C_1(x)^2 + d*C_1(x)^3 + e*C_2(x) + f*C_2(x)^2 + g*C_2(x)^3]$$

Where $C_1$ is based on the total T detector array and the set of outer detectors X and $C_2$ is based on the total T detector array and the original set of outer detectors O. Accordingly, it can be seen that the number of sets of outer detectors can be expanded until no further improvement is added to the compensated weight value. This aspect of the invention is believed to be particularly applicable to other than paper webs, for example in alloy compensation in flat sheet metal webs.

Although the invention has been described with particular reference to certain illustrated embodiments thereof, variations and modifications of the present invention can be effected within the spirit and scope of the following claims.

What is claimed is:

1. Apparatus for measuring a characteristic of a web of material by detecting a beta radiation beam after passage through said web of material comprising:
   a first detector generally aligned with a beta radiation beam to be detected and generating a first signal representative of a first portion of said beam received by said first detector;
   a second detector at least partially surrounding said first detector and generating a second signal representative of a second portion of said beam received by said second detector; and
   a controller receiving said first and second signals and generating a first characteristic signal from said first signal, a second characteristic signal from said second signal and a third characteristic signal from a combination of said first and second signals, wherein said first and second characteristic signals are used to compensate said third characteristic signal for variations in atomic composition of said web of material through which said beta radiation beam passes.

2. Apparatus for measuring a characteristic of a web of material by detecting a beta radiation beam after passage through said web of material comprising:
   a first detector generally aligned with a beta radiation beam to be detected and generating a first signal representative of a first portion of said beam received by said first detector;
   a second detector at least partially surrounding said first detector and generating a second signal representative of a second portion of said beam received by said second detector;
   at least a third detector at least partially surrounding said first detector and said second detector and generating a third signal representative of a third portion of said beam received by said third detector; and
   a controller receiving said first, second and third signals and generating a first characteristic signal from said first signal, a second characteristic signal from said second signal and a third characteristic signal from said third signal, said controller further generating a fourth characteristic signal from a combination of said first, second and third signals, wherein said first, second and third signals are used to compensate said fourth characteristic signal for variations in atomic composition of said web of material through which said beta radiation beam passes.

3. Apparatus as claimed in claim 1 wherein said characteristic is area weight of said web of material.

4. Apparatus as claimed in claim 1 wherein said first detector comprises a first plurality of individual beta detectors and said second detector comprises a second plurality of individual beta detectors.

5. Apparatus as claimed in claim 1 wherein said first and second detectors comprise an array of individual beta detectors.

6. Apparatus as claimed in claim 5 wherein said first detector comprises a plurality of individual beta detectors of an inner portion of said array and said second detector comprises a plurality of individual beta detectors of an outer portion of said array.

7. Apparatus as claimed in claim 6 wherein said plurality of individual beta detectors of an outer portion of said array at least partially surround said plurality of individual beta detectors of an inner portion of said array.

8. Apparatus as claimed in claim 7 wherein said plurality of individual beta detectors of an outer portion of said array surround said plurality of individual beta detectors of an inner portion of said array.

9. A method for measuring a characteristic of a web of material by detecting a beta radiation beam after passage through said web of material comprising:
   generating a first signal representative of a first portion of said beam received by a first detector;
   generating a second signal representative of a second portion of said beam received by a second detector;
   generating a first characteristic signal from said first signal;
   generating a second characteristic signal from said second signal;
   generating a third characteristic signal from a combination of said first and second signals; and
   using said first and second characteristic signals to compensate said third characteristic signal for variations in atomic composition of said web of material through which said beta radiation beam passes.

10. A method for measuring a characteristic of a web of material by detecting a beta radiation beam after passage through said web of material comprising:
- generating a first signal representative of a first portion of said beam received by a first detector;
- generating a second signal representative of a second portion of said beam received by a second detector;
- generating at least a third signal representative of a third portion of said beam received by a third detector;
- generating a first characteristic signal from said first signal;
- generating a second characteristic signal from said second signal;
- generating a third characteristic signal from said third signal;
- generating a fourth characteristic signal from a combination of said first, second and third signals; and
- using said first, second and third characteristic signals to compensate said fourth characteristic signal for variations in atomic composition of said web of material through which said beta radiation beam passes.

11. A method for measuring a characteristic of a web of material as claimed in claim 9 further comprising:
- generally aligning said first detector with said beam; and
- at least partially surrounding said first detector with said second detector.

12. A method for measuring a characteristic of a web of material as claimed in claim 9 further comprising:
- forming said first detector as a first plurality of individual detectors; and
- forming said second detector as a second plurality of individual detectors.

13. A method for measuring a characteristic of a web of material as claimed in claim 9 further comprising:
- providing a plurality of individual detectors;
- defining said first detector as a first electrically selectable portion of said plurality of individual detectors; and
- defining said second detector as a second electrically selectable portion of said plurality of individual detectors.

14. A method for measuring a characteristic of a web of material as claimed in claim 13 further comprising:
- generally aligning said first portion of said plurality of individual detectors with said beam; and
- at least partially surrounding said first portion of said plurality of individual detectors with said second portion of said plurality of individual detectors.

15. A method for measuring a characteristic of a web of material by detecting a beta radiation beam after passage through said web of material comprising:
- generating a first signal representative of a first portion of said beam received by a first detector;
- generating a second signal representative of a second portion of said beam received by a second detector;
- measuring a characteristic of an array of first calibration samples with said first detector;
- measuring said characteristic of said array of first calibration samples with said second detector;
- measuring said characteristic of said array of first calibration samples with a combination of said first and second detectors;
- calibrating said first detector, said second detector and said combination of said first and second detectors so that each of said first detector, said second detector and said combination of said first and second detectors accurately measure said characteristic of said array of first calibration samples;
- measuring said characteristic of an array of second calibration samples with said first detector, said array of second calibration samples having a higher atomic number than said array of first calibration samples;
- measuring said characteristic of said array of second calibration samples with said second detector;
- measuring said characteristic of said array of second calibration samples with a combination of said first and second detectors;
- determining a measurement error array equal to a difference between measurements of said characteristic of said array of second calibration samples with a combination of said first and second detectors and laboratory values for said array of second calibration samples;
- determining a correction signal array equal to a difference between measurements of said characteristic by said first detector and measurements of said characteristic by said second detector;
- correlating said measurement error array with said correction signal array to determine measurement errors to be subtracted from characteristic measurements made with a combination of said first and second detectors; and
- subtracting said measurement errors from said measurements made with a combination of said first and second detectors to determine compensated measurements of said characteristic.

16. A method for measuring a characteristic of a web of material as claimed in claim 15 wherein correlating said measurement error array with said correction signal array to determine measurement errors to be subtracted from characteristic measurements made with a combination of said first and second detectors comprises curve fitting said correction signal array to said measurement error array.

17. A method for measuring a characteristic of a web of material as claimed in claim 16 wherein said curve fitting comprises using a third order polynomial to fit said correction signal array to said measurement error array.

18. Apparatus for measuring a characteristic of a web of material by detecting a beta radiation beam after passage through said web of material comprising:
- an inner detector generally aligned with a beta radiation beam to be detected and generating an inner signal representative of an inner portion of said beam received by said first detector;
- at least one outer detector at least partially surrounding said inner detector and generating a corresponding outer signal representative of an outer portion of said beam received by said at least one outer detector; and
- a controller receiving said inner and outer signals and generating an inner characteristic signal from said inner signal, an outer characteristic signal from said outer signal and a combined characteristic signal from a combination of said inner and outer signals, wherein said inner and outer characteristic signals are used to compensate said combined characteristic signal for variations in atomic composition of said web of material through which said beta radiation beam passes.

19. Apparatus for measuring a characteristic of a web of material as claimed in claim 18 comprising at least first and second outer detectors.

20. A method for measuring a characteristic of a web of material by detecting a beta radiation beam after passage through said web of material comprising:

generating an inner signal representative of an inner portion of said beam received by an inner detector;

generating at least one outer signal representative of a corresponding portion of said beam received by at least one corresponding outer detector;

generating an inner characteristic signal from said inner signal;

generating at least one outer characteristic signal from said at least one outer signal;

generating a combined characteristic signal from a combination of said inner and outer signals; and using said inner and outer characteristic signals to compensate said combined characteristic signal for variations in atomic composition of said web of material through which said beta radiation beam passes.

\* \* \* \* \*

UNITED STATES PATENT AND TRADEMARK OFFICE
CERTIFICATE OF CORRECTION

PATENT NO.        : 7,005,639 B2                                    Page 1 of 1
APPLICATION NO. : 10/628197
DATED             : February 28, 2006
INVENTOR(S)      : Steven Perry Sturm It is certified that error appears in the above-identified patent and that said Letters Patent is hereby corrected as shown below:

<u>Column 5,</u>
Line 5, "signal arrays, S2oa, 32oo and" should read -- signal arrays, 32oa, 32oo and --;
Line 40, "ST(X) is an array" should read -- ST(x) is an array --;
Line 54, "signal arrays, ST(X)," should read -- signal arrays, ST(x) --;

<u>Column 7,</u>
Line 21, "$Wt(x) \approx SWt_T(x) \approx SWt_o(x) + SWt_1(x)$" should read
-- $Wt(x) \approx SWt_T(x) \approx SWt_o(x) \approx SWt_1(x)$ --.

Signed and Sealed this

Eleventh Day of July, 2006

JON W. DUDAS
*Director of the United States Patent and Trademark Office*